United States Patent [19]
Allen, Jr.

[11] Patent Number: 4,602,628
[45] Date of Patent: Jul. 29, 1986

[54] CRYOGENIC EXTRACTOR AND FILLER

[76] Inventor: Robert E. Allen, Jr., 2041 Buckingham Ct., Decatur, Ga. 30035

[21] Appl. No.: 692,663

[22] Filed: Jan. 17, 1985

[51] Int. Cl.4 ............................................. A61B 17/36
[52] U.S. Cl. ..................... 128/303.1; 62/293
[58] Field of Search ....................... 128/303.1; 62/293

[56] References Cited

U.S. PATENT DOCUMENTS

| | | | |
|---|---|---|---|
| 2,746,264 | 5/1956 | Keyes | 128/303.1 |
| 3,259,131 | 7/1966 | Kanbar et al. | 128/303.1 |
| 3,343,544 | 9/1967 | Dunn et al. | 128/303.1 |
| 3,425,417 | 2/1969 | Kanbar et al. | 128/303.1 |
| 3,434,477 | 3/1969 | Thomas, Jr. | 128/303.1 |
| 3,575,176 | 4/1971 | Crump et al. | 128/303.1 |
| 3,795,245 | 3/1974 | Allen, Jr. | 128/303.1 |
| 3,830,239 | 8/1974 | Stumpf | 128/303.1 |
| 3,910,278 | 10/1975 | Crandell et al. | 128/303.1 |
| 3,951,152 | 4/1976 | Crandell et al. | 128/303.1 |

*Primary Examiner*—Paul J. Hirsch
*Attorney, Agent, or Firm*—James B. Middleton

[57] ABSTRACT

A cryogenic extractor having a self-contained filler, and a tip activated by slanting the tip down. A cryogenic extractor has a foward chamber having a rod to be cooled, the rod extending adjacent to the top wall so the liquid will not reach the rod when the extractor is held horizontally with the bottom down. The extractor has a rear chamber for receiving the liquid refrigerant on filling. A filling cartridge is received in the rear chamber, and a base holds the cartridge. The base receives the skirt of the rear chamber on one step for shipping, and on another, lower step for use. The skirt must be forced over the lower step, and the fit holds the skirt in place and, provides a tight seal. An activator on the cartridge is pushed down when the extractor is pushed down, dispensing the refrigerant from the cartridge, and the refrigerant flows down into the rear chamber. The extractor can be tipped to a horizontal position and rested on the bottom without activating the tip, and further slanting of the extractor will cause the liquid to engage the metal rod to activate the tip.

9 Claims, 6 Drawing Figures

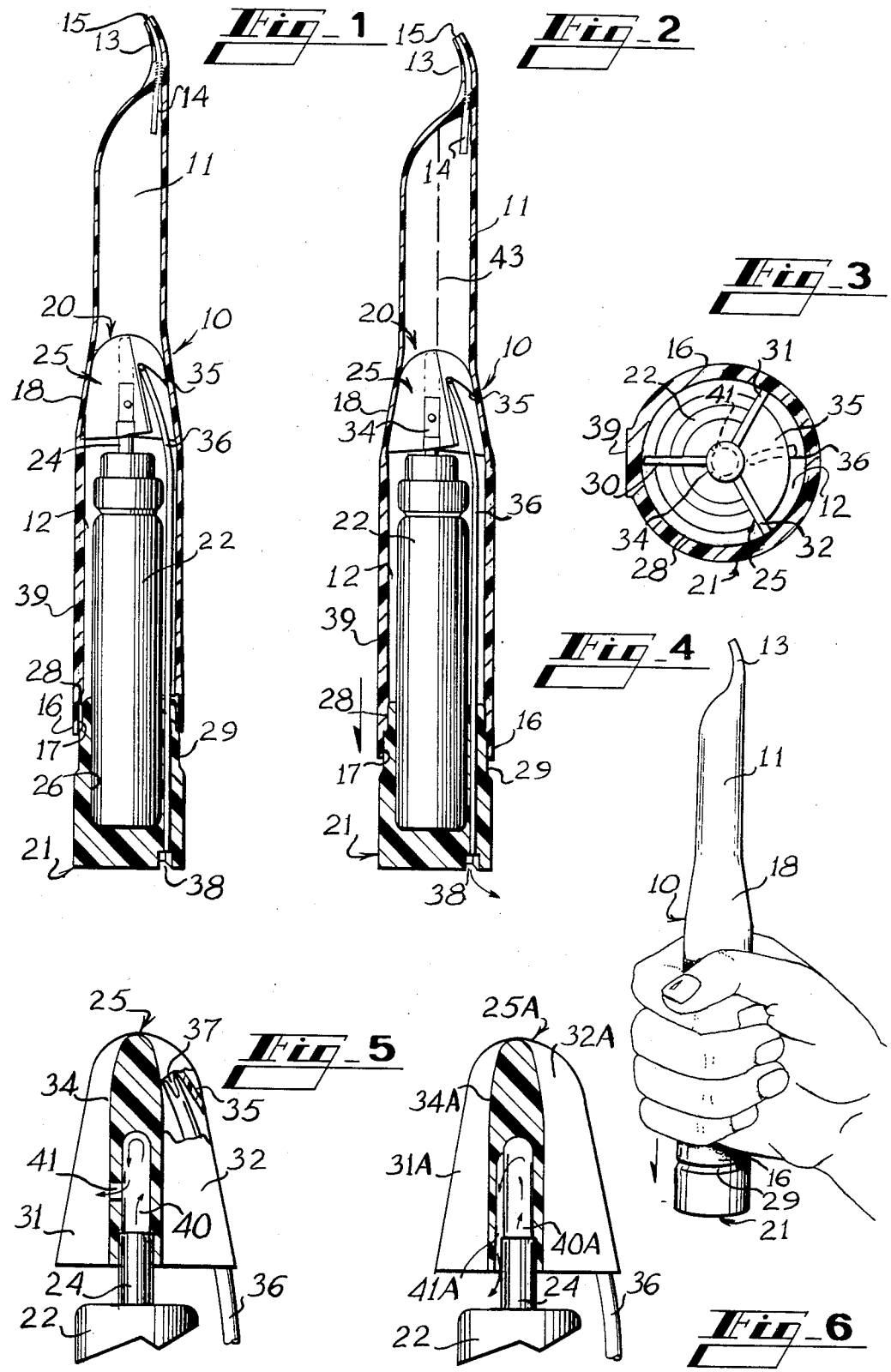

CRYOGENIC EXTRACTOR AND FILLER

INFORMATION DISCLOSURE STATEMENT

It is known in the art to utilize a cryogenic extractor in removing the lens from an eye. Whereas prior techniques involve removal of the lens using forceps and the like, later techniques involve the use of the cryogenic extractor wherein a metal tip is cooled to a below-freezing temperature and is placed into contact with the lens. The moisture on the lens causes the lens to freeze to the metal tip, allowing the lens to be held securely and pulled from the chamber.

Such cryogenic extractors have met with some commercial success, but there is a continuing problem in appropriately filling the extractor with the cooling fluid while permitting evaporation of the gas and prohibiting leakage of the liquid refrigerant. A conventional cryogenic extractor is shown in U.S. Pat. No. 3,795,245 issued Mar. 5, 1974. The device disclosed in this patent requires the use of a separate filling means for filling the extractor itself. This of course is unhandy, and may lead to premature activation of the cryogenic extractor, which may cause the formation of ice on the tip before use. While other cryogenic extractors involve somewhat different filling means, there is no completely self-contained filler for easy filling of the extractor which prevents premature activation of the tip.

SUMMARY OF THE INVENTION

This invention relates generally to cryogenic extractors, and is more particularly concerned with a cryogenic extractor having a filling means operable by the surgeon immediately before use, the extractor being arranged to prevent inadvertent activation.

The present invention provides, for use in conjunction with a generally conventional cryogenic extractor, a filling apparatus including a cartridge containing the fluid refrigerant, and a base container for receiving the cartridge. An actuator for the cartridge is mounted on the eduction tube of the cartridge, and is arranged to operate the conventional valve in the cartridge on being depressed. The actuator is arranged both to actuate the cartridge, and to direct the resulting flow of fluid. The actuator further includes a vent tube baffle. One end of the vent tube is received within the baffle to prevent liquid refrigerant from contacting the end of the tube, and the vent tube extends into the base to exhaust the interior of the extractor to the atmosphere. A flat bottom on the extractor allows the extractor to be rested on a surface, the extractor being arranged so the tip will not be activated without further tipping.

In its preferred form, the filling apparatus will be received within the container portion of the extractor, all parts being secure so the valve of the refrigerant cartridge will not be opened inadvertently. When the extractor is to be filled, the surgeon can force the extractor downwardly on the base, and this action will cause the actuator to be depressed, opening the valve in the refrigerant cartridge and causing the contents to be dispensed into the interior of the extractor. The liquid will be directed downwardly, the extracting tip being up so that the extractor is not activated during the filling of the extractor. Only when the instrument is to be activated will the extractor be tipped carefully, the extractor tip being lowered beyond a horizontal attitude, allowing the liquid to run past the actuator and to the tip of the extractor to activate the extractor.

BRIEF DESCRIPTION OF THE DRAWINGS

These and other features and advantages of the present invention will become apparent from consideration of the following specification when taken in conjunction with the accompanying drawings in which:

FIG. 1 is a longitudinal cross-sectional view of a cryogenic extractor made in accordance with the present invention, the extractor being shown before the filling device is actuated to fill the extractor;

FIG. 2 is a view similar to FIG. 1, but showing the device after filling;

FIG. 3 is a top plan view of the filling apparatus of the present invention, with the extractor cut away to reveal the entire filling apparatus;

FIG. 4 is an illustration showing the actuating of the filling apparatus contained in the extractor;

FIG. 5 is an enlarged cross-sectional view taken through the actuator and showing the exit port for the liquid refrigerant; and, FIG. 6 is a view similar to FIG. 5, and showing an alternate construction.

DETAILED DESCRIPTION OF THE EMBODIMENTS

Referring now more particularly to the drawings, and to those embodiments here presented by way of illustration, it will be seen that FIG. 1 illustrates a generally conventional cryoextractor designated at 10 having a forward chamber 11 and a rear chamber 12. The forward chamber 11 terminates in the extractor tip 13 which includes a metal rod 14. Those skilled in the art will understand that the extractor 10 will generally be made of a plastic material such as polypropylene or the like, and the metal rod 14 will be surrounded in plastic with the tip 15 exposed. Due to this arrangement, when a refrigerant is placed into the forward chamber 11, the refrigerant contacts the metal rod 14, and the cooling of the rod 14 cools the tip 15 to a temperature that will cause rapid freezing of any moisture that contacts the tip 15.

While some prior art extractors have a forward chamber 11 with a configuration similar to that here illustrated, it will be noticed that there is an important difference. The rod 14 is normally angled towards the bottom of the extractor, or the left as shown in FIGS. 1 and 2, in an effort to be sure the rod 14 is contacted by the refrigerant when the refrigerant is in the chamber 11. Contrarily, the rod 14 in the present invention remains adjacent to the top, or right side as viewed in FIGS. 1 and 2.

As is discussed below, the extractor 10 includes a flat bottom 39. Because of the off set tip 13, and the placing of the rod 14 adjacent to the top of the extractor, the extractor 10 can be filled, as in FIG. 2, then placed on its flat bottom 39. The quantity of refrigerant is such that the liquid level will be generally along the broken line 43. As a result, the tip 15 will not be activated.

It will be seen that the rear chamber 12 is formed with a generally straight skirt 16, and there is a transition 18 between the rear chamber 12 and the forward chamber 11. This transition 18 is generally frustoconical, and this will be discussed further hereinafter.

The filling apparatus is generally designated at 20, and includes a base 21 for receiving a conventional refrigerant cartridge 22. The cartridge 22, as is conventional, includes a tubular stem 24 that can be depressed to release liquid from the cartridge 22, the liquid passing through the center of the tube 24 to be dispensed axially thereof. This tube 24 receives the baffle, or actuator, 25 of the present invention.

Referring again to the base 21, it will be seen that the base 21 includes a central opening 26 for receiving the cartridge 22. The cartridge 22 is received snugly within the opening 26 so inadvertent displacement is prevented. The outside of the base 21 includes a plurality of steps, the first, and smallest, step being designated at 28.

Looking further at FIG. 1, the skirt 16 of the extractor 10 is enlarged at its lower end as indicated at 17. The enlarged area 17 is dimensioned to be a very tight fit over the step 29 of the base 21, so that extractor will normally be held with respect to the base as shown in FIG. 1. In this condition, the baffle 25 is sufficiently forward that the valve of the refrigerant cartridge is not operated. The extractor 10 can be shipped and otherwise safely handled in this condition.

Looking at FIG. 2 of the drawings, it will be seen that the extractor is previsely the same as is shown in FIG. 1, but the skirt 16 has been moved downwardly to the next step 29. The enlarged area 17 of the skirt 16 will be so sized with respect to the step 29 that a very snug fit will be achieved, and the skirt will engage the step 28 as shown. The snug fit is both to hold the skirt 16 in place and to achieve a sufficient seal to prevent leakage of the liquid refrigerant from the rear chamber 12 of the extractor 10.

When the skirt 16 is moved downwardly to overlap the step 29, it will be seen that the transition 18 also moves downwardly, and it is this motion that actuates the filling apparatus 20 by urging the actuator 25 downwardly.

Looking at the actuator 25 in more detail, it will be seen that the actuator includes three flanges 30, 31 and 32 arranged equi-angularly about a hub 34. The hub 34 has a central passage therein for receiving the tube 24, and includes openings into the interior of the extractor 10.

Looking at FIG. 3 of the drawings, it will be seen that there is a vent tube shield or baffle 35 extending between the flanges 31 and 32. Considering FIG. 3 in conjunction with FIGS. 1 and 2, it will be seen that the vent tube designated at 36 terminates beneath the shield 35, the shield 35 protecting the end of the vent tube, while the vent tube 36 extends downwardly, and into an appropriate opening in the base 21. There is then an exit port 38 for allowing gas to escape from the extractor 10.

Looking further at FIG. 3 of the drawings, it will be seen that the skirt 16 of the rear chamber 12 is generally circular in cross-section, but includes a flat side designated at 39. It will further be seen that the flange 30 of the actuator 25 is arranged generally perpendicularly to the flat side 39. As will be more fully understood later, the flat side 39 constitutes a tactile clue for the proper orientation of the extractor 10, and the flange 30 should always be arranged as shwon in FIG. 3.

Looking now at FIG. 5 of the drawings for a better understanding of the operation of the actuator 25, it will be seen that the central passage 40 in the hub 34 is sized to receive the tube 24 of the cartridge 22. When the actuator 25 is depressed to depress the tube 24 and open the valve as is conventional, liquid refrigerant will pass through the tube 24 and into the opening 40 in the hub 34. In the embodiment shown in FIG. 5, there is an exit hole 41 through which the liquid will escape. In FIG. 3, it will be understood that the hole 41 is between the flanges 30 and 31, and there will preferably be a second hole in the hub between the flanges 30 and 32.

Because of the particular arrangement, it will be seen that, when the liquid is expelled through the hole such as the hole 41, the liquid will engage the inner wall of the transition 18 and be deflected downwardly. As a result, the liquid will partially fill the rear chamber 12 of the extractor 10, and liquid will not pass into the forward chamber 11 so the tip of the extractor cannot be activated. The tip of the vent tube 36 is well protected between the flanges 31 and 32 and beneath the shield 35, so liquid will not pass through the vent tube 36; however, the vent tube 36 is notched as shown at 37 in FIG. 5 to be sure gas can enter the tube 36. The notch 37 prevents undue restriction by the shield 35.

Looking now at FIG. 6 of the drawings, there is a modified form of actuator indicated at 25A, the actuator 25A having flanges 31A and 32A with a hub 34A having a central opening 40A. The tube 24 of the refrigerant cartridge 22 is to be received within the central opening 40A as before. The difference is the exit means for the liquid from the opening 40A. In the embodiment shown in FIG. 6 of the drawings, there is a keyway indicated at 41A, the keyway overlapping the tube 24 and extending therebeyond. As a result, when the liquid is received within the channel 40A, the liquid can pass through the keyway 41A and out into the rear chamber 12. With the embodiment shown in FIG. 6 of the drawings, it will be understood that the liquid is directed in a definitely downward direction to assist in preventing liquid from passing into the forward chamber 11 of the extractor 10.

From the foregoing description, operation of the device should now be understandable. Looking at FIG. 4 of the drawings, it will be seen that the extractor 10 can be seated on its base 21, the refrigerant being completely contained within the refrigerant cartridge 22. When the surgeon believes he will need the extractor shortly, the extractor can be grasped as shown in FIG. 4, and the body of the extractor 10 urged downwardly, forcing the enlarged area 17 of the skirt 16 over the step 29 of the base 21. This motion will also cause the transition 18 to engage the flanges 30, 31 and 32 of the actuator 25, pushing the tube 24 downwardly to open the valve within the refrigerant cartridge and causing liquid to pass from the cartridge, through the tube 24 and into the central opening 40 or 40A. The liquid will then pass through the opening 41 or 41A and into the rear chamber 12. In this condition, the extractor 10 can be allowed to rest for a reasonable length of time. There is no danger that the tip 15 will be activated until the instrument is tipped over with the tip 13 below the horizontal plane, so the limiting factor is only loss of refrigerant through normal heat transfer and resulting evaporation.

The flat portion 39 of the skirt 16 will indicate to the surgeon the bottom of the extractor 10, and a similar flat portion on the base 21 provides for proper alignment of the base with the extractor, hence proper alignment of the flange 30 with the flat 39. Thus, the surgeon can feel the position of the extractor; and, when the extractor is to be activated, the flat portion 39 will be kept down and the instrument slowly tipped over so that liquid will run along the bottom of the instrument, which is the left-hand side of the instrument as shown in the drawings. It will be seen that the flange 30 on the actuator 25 will allow the liquid to flow past without noticeable obstruction. Also, when the instrument is tipped slowly, the liquid will not rise to a sufficient level to flow behind the shield 35, so the liquid avoids the vent tube 36. Further, the instrument can be tipped over to only a horizontal position, and the liquid will lie on the line 43 so the tip 13 will not yet be activated.

As the instrument is tipped completely forward, below the horizontal plane, it will be understood that the liquid refrigerant will flow within the forward chamber 11 and contact the rod 14. At this point, the heat will be transferred from the rod 14 into the refrigerant, causing increased boiling and evaporation of the refrigerant and cooling of the rod 14, hence the tip 15.

It will therefore be understood that the present invention provides an extremely simple apparatus for filling a cryogenic extractor, the device being such as to be manufactured from molded plastic or the like, resulting in a sufficiently inexpensive arrangement as to allow the device to be disposable. While a particular form of actuator is here illustrated, it will be apparent that many modifications can be made, the object being to allow protection of the vent tube, actuation of the refrigerant cartridge, and passage of the liquid during tipping of the instrument.

It will therefore be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as defined in the appended claims.

I claim:

1. In a cryogenic extractor having filling apparatus, said extractor including a forward chamber, a rear chamber generally coaxial with said forward chamber, a transition between said forward chamber and said rear chamber, a tip at the forwardmost end of said forward chamber, said tip including a metal rod to be cooled by contact with a refrigerant, said filling apparatus including a cartridge containing a refrigerant, said cartridge being received within said rear chamber of said extractor, and means for dispensing the refrigerant in said cartridge into said rear chamber, the improvement wherein said filling apparatus includes a base, said base defining a central cavity for receiving said cartridge, said base being receivable within the rearmost end of said rear chamber, an actuator for said cartridge, said base defining a first step for normally receiving the end of said rear chamber, and a second step rearwardly of said first step, said second step being so dimensioned with respect to said rear chamber that said rear chamber can be forcefully urged downwardly to seat on said second step and form a secure seal between said base and said rear chamber, said actuator being located within said transition and being engageable by said transition as said rear chamber moves down onto said second step, the arrangement being such that downward motion of said rear chamber actuates said cartridge to dispense said refrigerant and simultaneously seals said rear chamber.

2. In a cryogenic extractor as claimed in claim 1, said actuator including a plurality of flanges extending generally radially of said transition for engaging said transition, a hub centrally of said flanges and fixed thereto, the arrangement being such that said actuator is held in position within said transition while allowing fluid to flow past said actuator.

3. In a cryogenic extractor as claimed in claim 2, the improvement wherein said hub defines a central chamber for receiving said refrigerant from said cartridge, and means for directing said refrigerant into said rear chamber.

4. In a cryogenic extractor as claimed in claim 3, said actuator including a shield extending between two adjacent flanges, a vent tube terminating beneath said shield and extending into said base, the arrangement being such that said vent tube is shielded to prevent loss of liquid therethrough while allowing gas to pass therethrough.

5. In a cryogenic extractor as claimed in claim 1, said actuator including a hub, said cartridge having a stem through which refrigerant can be dispensed from said cartridge, said hub defining a central opening for receiving said stem, a plurality of flanges extending radially from said hub for positioning said hub axially of said transition, and a dispensing opening connecting said central opening in said hub with said rear chamber of said extractor.

6. In an extractor as claimed in claim 5, one flange of said plurality of flanges extending in a first direction, a flat side on said rear chamber in said first direction, said flat side constituting a bottom for said extractor.

7. In an extractor as claimed in claim 6, a shield extending between two flanges of said actuator, a vent tube extending from said base and terminating beneath said shield, so that said vent tube extends opposite said flat side, the arrangement being such that said rear chamber will contain liquid refrigerant and said extractor will be tipped over with said bottom downward, liquid passing said one flange and avoiding contact with said vent tube, and further, said shield will protect said vent tube from receiving liquid when said extractor is replaced on said base.

8. In a cryogenic extractor as claimed in claim 7, the further improvement wherein said extractor includes a bottom wall constituting said bottom and a top wall, said metal rod extending into said forward chamber and being adjacent to, and generally parallel to, said top wall, the arrangement being such that said extractor can be disposed horizontally with said bottom wall down, and the refrigerant will not engage said metal rod.

9. A cryogenic extractor comprising a container, a tip at the forward end of said container, said tip including a metal rod to be cooled by contact with a refrigerant, and filling means for placing a quantity of liquid refrigerant into said container, said extractor having a flat bottom wall, and a top wall, said botttom wall and top wall being generally parallel to each other and extending longitudinally of said container, said metal rod extending from said tip into said container and lying adjacent to, and generally parallel to, said top wall, said quantity of liquid refrigerant being such that the liquid refrigerant will not engage said metal rod when said extractor is resting on said flat bottom wall.

* * * * *